(12) United States Patent
Whiteford et al.

(10) Patent No.: US 8,088,483 B1
(45) Date of Patent: *Jan. 3, 2012

(54) PROCESS FOR GROUP 10 METAL NANOSTRUCTURE SYNTHESIS AND COMPOSITIONS MADE USING SAME

(75) Inventors: Jeffery A. Whiteford, Belmont, CA (US); Mihai A. Buretea, San Francisco, CA (US); William P. Freeman, San Mateo, CA (US); J. Wallace Parce, Palo Alto, CA (US); Baixin Qian, Sunnyvale, CA (US); Erik C. Scher, San Francisco, CA (US)

(73) Assignee: Nanosys, Inc., Palo Alto, CA (US)

( * ) Notice: Subject to any disclaimer, the term of this patent is extended or adjusted under 35 U.S.C. 154(b) by 1462 days.

This patent is subject to a terminal disclaimer.

(21) Appl. No.: 11/304,498

(22) Filed: Dec. 15, 2005

Related U.S. Application Data

(63) Continuation-in-part of application No. 11/299,299, filed on Dec. 9, 2005, which is a continuation-in-part of application No. 11/147,670, filed on Jun. 7, 2005, now Pat. No. 7,267,875.

(60) Provisional application No. 60/637,409, filed on Dec. 16, 2004, provisional application No. 60/578,236, filed on Jun. 8, 2004, provisional application No. 60/632,570, filed on Nov. 30, 2004.

(51) Int. Cl.
*B32B 5/66* (2006.01)
(52) U.S. Cl. ........ 428/402; 428/403; 428/407; 427/384; 427/387; 427/372.2
(58) Field of Classification Search .................. 428/402, 428/403, 407; 427/384, 387, 372.2
See application file for complete search history.

(56) References Cited

U.S. PATENT DOCUMENTS

| | | |
|---|---|---|
| 5,043,940 A | 8/1991 | Harari |
| 5,434,825 A | 7/1995 | Harari |
| 5,505,928 A | 4/1996 | Alivisatos et al. |
| 5,690,807 A | 11/1997 | Clark, Jr. et al. |
| 5,714,766 A | 2/1998 | Chen et al. |
| 5,751,018 A | 5/1998 | Alivisatos et al. |
| 5,897,945 A | 4/1999 | Lieber et al. |
| 5,937,295 A | 8/1999 | Chen et al. |
| 5,990,479 A | 11/1999 | Weiss et al. |
| 5,997,832 A | 12/1999 | Lieber et al. |
| 6,036,774 A | 3/2000 | Lieber et al. |
| 6,048,616 A | 4/2000 | Gallagher et al. |
| 6,054,349 A | 4/2000 | Nakajima et al. |
| 6,090,666 A | 7/2000 | Ueda et al. |
| 6,136,156 A | 10/2000 | El-Shall et al. |
| 6,139,626 A | 10/2000 | Norris et al. |
| 6,159,620 A | 12/2000 | Heath et al. |
| 6,207,229 B1 | 3/2001 | Bawendi et al. |
| 6,222,762 B1 | 4/2001 | Guterman et al. |
| 6,225,198 B1 | 5/2001 | Alivisatos et al. |
| 6,275,419 B1 | 8/2001 | Guterman et al. |
| 6,306,736 B1 | 10/2001 | Alivisatos et al. |
| 6,317,363 B1 | 11/2001 | Guterman et al. |
| 6,317,364 B1 | 11/2001 | Guterman et al. |
| 6,322,901 B1 | 11/2001 | Bawendi et al. |
| 6,344,403 B1 | 2/2002 | Madhukar et al. |
| 6,413,489 B1 | 7/2002 | Ying et al. |
| 6,413,819 B1 | 7/2002 | Zafar et al. |
| 6,576,291 B2 | 6/2003 | Bawendi et al. |
| 6,577,532 B1 | 6/2003 | Chevallier |
| 6,586,785 B2 | 7/2003 | Flagan et al. |
| 6,723,606 B2 | 4/2004 | Flagan et al. |
| 6,781,166 B2 | 8/2004 | Lieber et al. |
| 6,872,645 B2 | 3/2005 | Duan et al. |
| 6,878,871 B2 | 4/2005 | Scher et al. |
| 6,949,206 B2 | 9/2005 | Whiteford et al. |
| 7,091,120 B2 | 8/2006 | Buretea et al. |
| 7,267,875 B2 * | 9/2007 | Whiteford et al. ............. 428/402 |
| 7,585,564 B2 * | 9/2009 | Whiteford et al. ............. 428/402 |
| 7,713,955 B2 * | 5/2010 | Whiteford et al. ............. 514/183 |
| 2002/0066401 A1 | 6/2002 | Peng et al. |
| 2002/0071952 A1 | 6/2002 | Bawendi et al. |
| 2002/0117659 A1 | 8/2002 | Lieber et al. |
| 2002/0130311 A1 | 9/2002 | Lieber et al. |
| 2003/0173541 A1 | 9/2003 | Peng et al. |
| 2004/0023010 A1 | 2/2004 | Bulovic et al. |
| 2004/0026684 A1 | 2/2004 | Empedocles |
| 2004/0130941 A1 | 7/2004 | Kan et al. |
| 2005/0072989 A1 | 4/2005 | Bawendi et al. |
| 2005/0109989 A1 | 5/2005 | Whiteford et al. |
| 2005/0122775 A1 | 6/2005 | Koyanagi et al. |
| 2005/0201149 A1 | 9/2005 | Duan et al. |
| 2005/0202615 A1 | 9/2005 | Duan et al. |
| 2005/0287717 A1 | 12/2005 | Heald |
| 2006/0040103 A1 | 2/2006 | Whiteford et al. |

OTHER PUBLICATIONS

Ahmadi et al. "'Cubic' colloidal platinum nanoparticles" Chem Mater (1996) 8:1161-1163.
Ahmadi et al. "Shape-controlled synthesis of colloidal platinum nanoparticles" Science (1996) 272:1924-1926.
Atwater, H.A. "Silicon nanoparticle engineering for novel logic and memory applications" Project Overview, Functional Nanostructures Program, NSF (Jan. 2001).
Bell, L.D. et al., "A Radiation-tolerant, low-power non-volatile memory based on silicon nanocrystal quantum dots" Innovative Approaches to Outer Planetary Exploration 2001-2020 (Publication date unknown). Bjork, M.T. et al. "One-dimensional steeplechase for electrons realized" Nano Letters (2002) 2:86-90.
Bodefield, M.C. et al., "Storage of electrons and holes in self-assembled InAs quantum dots" Appl. Phys. Lett. (1999) 74(13):1839-1841.
Brown, J.F. et al. "Preparation and characterization of the lower equilibrated phenylsilsesquioxanes" J. Am. Chem. Soc.(1964) 86:1120-1125.
Brown, J.F. et al. "The polycondensation of cyclohexylsilanetriol" J. Am. Chem. Soc. (1965) 87:4313-4323.
Bulgakov, A.V. et al. "Laser ablation synthesis of zinc oxide clusters: a new family of fullerenes?" Chem. Phys. Lett. (2000) 320:19-25.

(Continued)

*Primary Examiner* — Leszek Kiliman
(74) *Attorney, Agent, or Firm* — Andrew L. Filler

(57) ABSTRACT

Methods for producing Group 10 metal nanostructures are provided. The methods involve novel precursors, novel surfactants, or novel precursor-surfactant combinations. Compositions related to the methods are also featured.

13 Claims, 4 Drawing Sheets

OTHER PUBLICATIONS

Cao, Y.W. et al. "Growth and properties of semiconductor core/shell nanocrystals with InAs cores" J. Am. Chem. Soc. (2000) 122:9692-9702.

Casperson, J.D. et al., "Materials issues for layered tunnel barrier structures" J. Appl. Phys. (2002) 92(1):261-267.

Chae, D-H et al., "Nanocrystal memory cell using high-density SiGe Quantum Dot Array" J Kor. Phys. Soc. (1999) 35:S995-S998.

Citeau, H. et al. "A novel cage organotellurate(IV) macrocyclic host encapsulating a bromide anion guest" Chem. Commun. (2001) pp. 2006-2007.

Coe, S. et al. "Electroluminescence from single monolayers of nanocrystals in molecular organic devices" Nature (2002) 450:800-803.

Coronado, E. et al. "Polyoxometalate-Based Molecular Materials" Chem. Rev. (1998) 98:273-296.

Corso, D. et al., "Localized Charge storage in nanocrystal memories: feasibility of a multi-bit cell" (Publication and Publication date unknown).

Cui, Y. et al. "Doping and electrical transport in silicon nanowires" J. Phys. Chem. B (2000) 104:5213-5216.

Cui, Y. et al. "Diameter-controlled synthesis of single-crystal silicon nanowires" Appl. Phys. Lett. (2001) 78:2214-2216.

Dabbousi, B.O. et al. "(CdSe)ZnS core-shell quantum dots: Synthesis and characterization of a size series of highly luminescent nanocrystallites" J. Phys. Chem. B (1997) 101:9463-9475.

De Blauwe, J. "Nanoparticle Nonvolatile Memory Devices," IEEE Trans. Nanotechnology (2002) 1:72-77.

Drexler, H. et al., "Spectroscopy of quantum levels in charge-tunable InGaAs quantum dots" Phys. Ref. Lett (1994) 73:2252-2255.

Driver et al. "A second-generation catalyst for aryl halide amination: Mixed secondary amines from aryl halides and primary amines catalyzed by (DPPF)PdCl2)" J Am Chem Soc (1996) 118:7217-7218.

Duan, X. et al. "General synthesis of compound semiconductor nanowires" Adv. Mater. (2000) 12:298-302.

Feher, F.J. et al. "Silsesquioxanes as models for silica surfaces" J. Am. Chem. Soc. (1989) 111:1741-1748.

Feher, F.J. et al. "Synthesis and characterization of vanadium-containing silsesquioxanes" Inorg. Chem. (1991) 30:1689-1694.

Feher, F.J. et al. "Silsesquioxanes as ligands in inorganic and organometallic chemistry" Polyhedron (1995) 14:3239-3253.

Gigant, K. et al. "Synthesis and Molecular Structures of Some New Titanium(IV) Aryloxides" J. Am. Chem. Soc. (2001) 123:11632-11637.

Gouzerh, P. et al. "Main-group element, organic, and organometallic derivatives of polyoxometalates" Chem. Rev. (1990) 98:77-111.

Green, M. et al., "Trialkylphosphine oxide/amine stabilised silver nanocrystals—the importance of steric factors and Lewis basicity in capping agents" J. Mat. Chem. (2002) 12:2671-2674.

Gudiksen, M.S. et al "Diameter-selective synthesis of semiconductor nanowires" J. Am. Chem. Soc. (2000) 122:8801-8802.

Gudiksen, M.S. et al. "Synthetic control of the diameter and length of single crystal semiconductor nanowires" J. Phys. Chem. B (2001) 105:4062-4064.

Gudiksen, M.S. et al. "Growth of nanowire superlattice structures for nanoscale photonics and electronics" Nature (2002) 415:617-620.

Gugliotti et al. "RNA-mediated metal-metal bond formation in the synthesis of hexagonal palladium nanoparticles" Science (2004) 304:850-852.

Hanssen, RWJM, "On the formation and reactivity of multinuclear silsesquioxane metal complexes" (2003) Dissertation Eindhoven University of Technology.

Iannaccone, G. et al., "Simulation of a quantum-dot flash memory," J. Appl. Phys. (1998) 84(9):5032-5036.

Ingelsten et al. "Kinetics of the formation of nano-sized platinum particles in water-in-oil microemulsions" J Colloid Interface Science (2001) 241:104-111.

Jun, Y-W et al. "Controlled synthesis of multi-armed CdS nanorod architectures using monosurfactant system" J. Am. Chem. Soc. (2001) 123:5150-5151.

Kan, E. "Technology for self-assembled entities in logic and memory units below the lithography limit" Cornell Nanoscale Facility (Publication date unknown).

Katsoulis, D.E. "A Survey of Applications of Polyoxometalates" Chem. Rev. (1998) 98:359-387.

Kim, S-W et al. "Synthesis of monodisperse palladium nanoparticles" NanoLetters (2003) 3:1289-1291.

Kolloipoulou, S. et al., "Hybrid silicon-organic nanoparticle memory device" J. Appl. Phys. (2003) 94(8):5234-5239.

Leaustic, A. et al. "Photochromism of cationic spiropyran-doped silica gel" New. J Chem. (2001) 25:1297-1301.

Lin, Y-H et al., "High-Performance Nonvolatile HfO2 Nanocrystal Memory" IEEE Electron Device Letts (Mar. 2005) 26(3):154-156.

Liu, C. et al. "Sol-Gel Synthesis of Free-Standing Ferroelectric Lead Zirconate Titanate Nanoparticles" J. Am. Chem. Soc. (2001) 123: 4344-4345.

Liu, C-M et al. "A novel bimetallic cage complex constructed from six V4Co pentatomic rings: hydrothermal synthesis and crystal structure of [(2,2'-Py2NH)2Co]3V8O23" Chem. Commun. (2001) pp. 1636-1637.

Louie et al. "Palladium-catalyzed synthesis of arylamines from aryl halides. Mechanistic studies lead to coupling in the absence of tin reagents" Tetrahedron Lett (1995) 36:3609-3612.

Manna, L. et al. "Synthesis of Soluble and Processable Rod-, Arrow-, Teardrop-, and Tetrapod-Shaped CdSe Nanocrystals" J. Am. Chem. Soc. (2000) 122:12700-12706.

Manna, L. et al. "Epitaxial growth and photochemical annealing of graded CdS/ZnS shells on colloidal CdSe nanorods" J. Am. Chem. Soc. (2002) 124:7136-7145.

Mccarthy, W., O'Reilly Network, "Quantum Dots and Programmable Matter" (visited Jan. 12, 2004) http://www.oreillynet.com/pub/a/network/2004/01/09/quantumdots.html, 5 pages, Copyright 2000-2004 O'Reilley & Associates, Inc.

Morales, A.M. et al. "A laser ablation method for the synthesis of crystalline semiconductor nanowires" Science (1998) 279:208-211.

Muller, A. et al. "Polyoxometalates" Very Large Clusters—Nanoscale Magnets Chem. Rev. (1998) 98:239-271.

Murray, C.B. et al., "Synthesis and characterization of nearly monodisperse CdE (E=S, Se, Te) semiconductor nanocrystals" J. Am. Chem. Soc. (1993) 115:8706-8715.

Paul et al. "Palladium-catalyzed formation of carbon-nitrogen bonds. Reaction intermediates and catalyst improvements in the hetero cross-coupling of aryl halides and tin amides" J Am Chem Soc (1994) 116:5969-5970.

Peng, X. et al. "Epitaxial growth of highly luminescent CdSe/CdS core/shell nanocrystals with photostability and electronic accessibility" J. Am. Chem. Soc. (1997).119:7019-7029.

Peng, X. et al. "Shape control of CdSe nanocrystals" Nature (2000) 404:59-61.

Pirmettis et al. "Synthesis and characterization of oxotechnetium(V) mixed-ligand complexes containing a tridentate N-substituted bis(2-mercaptoethyl)amine and a monodentate thiol" Inorg Chem (1996) 35:1685-1691.

Puntes, V.F. et al. "Colloidal nanocrystal shape and size control: The case of cobalt" Science (2001) 291:2115-2117.

Qu, L. et al. "Alternative routes toward high quality CdSe nanocrystals" NanoLetters (2001) 1:333-337.

Rhule, J.T. et al "Polyoxometalates in Medicine" Chem. Rev. (1998) 98:327-357.

Schmid, G. et al., "Silsesquioxanes as ligands for gold clusters" Eur. J. Inorg. Chem. (1998) 813-817.

Schubert, U. "Polymers Reinforced by Covalently Bonded Inorganic Clusters" Chem. Mater. (2001) 13:3487-3494.

Sellier, C. et al. "Crystal structure and charge order below the metal-insulator transition in the vanadium bronze β-SrV6O15" Solid State Sciences (2003) 5:591-599.

Son et al. "Facile synthesis of various phosphine-stabilized monodisperse palladium nanoparticles through understanding of coordination chemistry of the nanoparticles" Nano Letters (2004) 4:1147-1151.

Suzuki, A. "Recent Advanced in the Cross-Coupling Reactions of Organoboron Derivatives with Organic Electrophiles 1995-1998" J. Organomet. Chem. (1999) 576:147-168.

Takata, M. et al. "Fundamental characteristics of new non-volatile memory with extremely high density metal quantum dots" (Publication and Publication Date unknown).

Thomas et al. "From colloids to nanotechnology: Investigations of magic nuclearity palladium nanocrystals" Curr Sci (2003) 85:1760-1766.

Tiwari, S. et al., "Volatile and Non-Volatile Memories in Silicon with Nano-Crystal Storage," IEDM (1995) 95:521-527.

Tiwari, S. et al., "A silicon nanocrystals based memory" Appl. Phys. Lett (1996) 68(10):1377-1379.

Urban, J.J. et al. "Synthesis of single-crystalline perovskite nanowires composed of barium titanate and strontium titanate" J. Am. Chem. Soc. (2002) 124:1186-1187.

Vampola, K. et al., "Growth and Characterization of metal nanocrystals" Cornell Nanofabrication Facility (Publication date unknown).

Vargaftik, M.N. et al., "A Novel Giant Palladium Cluster" J. Chem. Soc. Chem. Commun. (1985) 937-939.

Weinstock, I.A. "Homogeneous-Phase Electron-Transfer Reactions of Polyoxometalates" Chem. Rev. (1998) 98:113-170.

Wolfe et al. "Palladium-catalyzed amination of aryl amines" J Org Chem (1996) 61:1133-1135.

Wu, Y. et al. "Block-by-block growth of single-crystalline Si/SiGe superlattice nanowires" Nano Letters (2002) 2:83-86.

Yamase, T. "Photo- and electrochromism of polyoxometalates and related materials" Chem. Rev. (1998) 98:307-325.

Yang, C-C. et al. "Characterization of poly(silsesquioxane) by thermal curing" Proc. Natl. Sci Counc. ROC (2001) 25:339-343.

Yee et al. One-phase synthesis of thiol-functionalized platinum nanoparticles Langmuir (1999) 15:4314-4316.

Yun, W.S. et al. "Ferroelectric Properties of Individual Barium Titanate Nanowires Investigated by Scanned Probe Microscopy" Nanoletters (2002) 2:447-450.

Zhang, K-Q. et al. "In situ observation of colloidal monolayer nucleation driven by an alternating electric field" Nature (2004) 429:739-743.

ISSCC delegates eye successor to floating gate flash memory http://www.electronicsweekly.com/article4907.htm Feb. 25, 2004.

Silicon Storage Technology, Inc. "Technical Comparison of Floating Gate Reprogrammable Nonvolatile Memories" Technical Paper, Nov. 2001 (Copyright 2002), 8 pages.

* cited by examiner

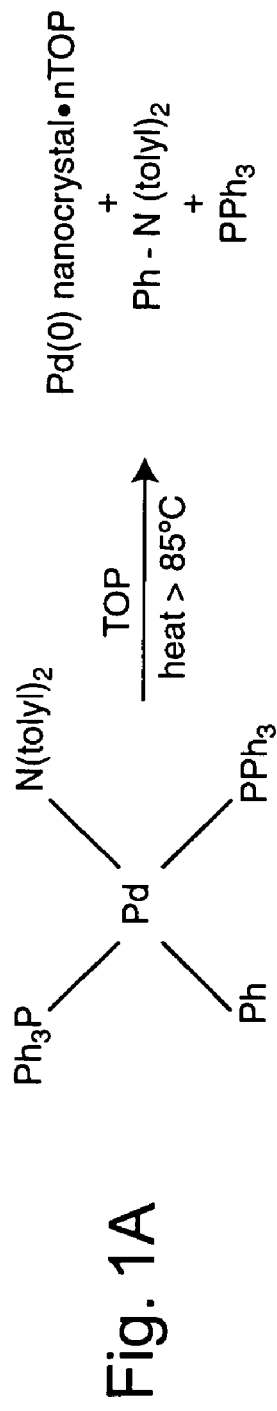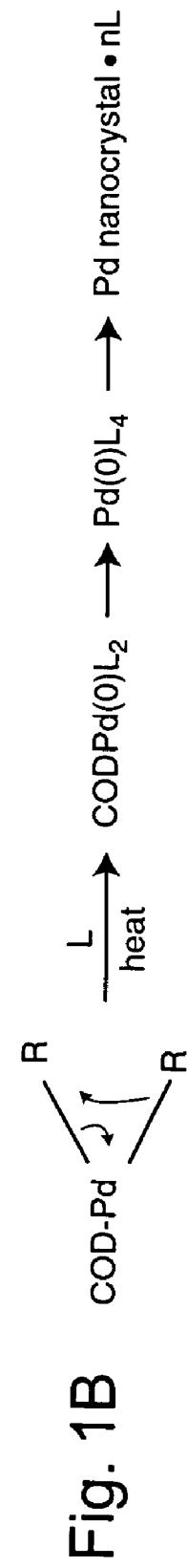

PROCESS FOR GROUP 10 METAL NANOSTRUCTURE SYNTHESIS AND COMPOSITIONS MADE USING SAME

CROSS-REFERENCE TO RELATED APPLICATION

This application claims priority to U.S. Provisional Application No. 60/637,409, filed Dec. 16, 2004, and is a continuation-in-part of U.S. patent application Ser. No. 11/299,299, filed Dec. 9, 2005, entitled "COMPOSITIONS AND METHODS FOR MODULATION OF NANOSTRUCTURE ENERGY LEVELS" which is a continuation-in-part of U.S. patent application Ser. No. 11/147,670, filed Jun. 7, 2005, which claims priority to and benefit of the following prior provisional patent applications: U.S. Ser. No. 60/578,236, filed Jun. 8, 2004, and U.S. Ser. No. 60/632,570, filed Nov. 30, 2004, each of which is incorporated herein by reference in its entirety for all purposes.

FIELD OF THE INVENTION

The invention is in the field of nanostructure synthesis. The invention relates to methods for producing nanostructures, particularly Group 10 metal nanostructures. The invention also relates to compositions useful in producing Group 10 metal nanostructures and compositions including Group 10 metal nanostructures.

BACKGROUND OF THE INVENTION

Group 10 metal nanostructures have uses ranging from catalysts and adsorbants to components of various optoelectronic devices. The properties of such nanostructures (e.g., their catalytic reactivity or electrical and optical properties) vary, e.g., depending on their composition, size, and shape. Methods for simply and reproducibly producing Group 10 metal nanostructures, e.g., of different sizes and/or shapes, are thus desirable. Among other aspects, the present invention provides such methods. A complete understanding of the invention will be obtained upon review of the following.

SUMMARY OF THE INVENTION

Methods for producing Group 10 metal nanostructures (Pd, Pt, and/or Ni nanostructures) are provided. The methods include, e.g., use of novel precursors, novel surfactants, or novel precursor-surfactant combinations. Related compositions are also described.

A first general class of embodiments provides methods for production of Group 10 metal nanostructures. In the methods, a precursor comprising a Group 10 atom selected from the group consisting of Pd, Pt, and Ni is provided and reacted to produce the nanostructures. The Group 10 atom can have an oxidation state of +2 and be bonded to one or more atoms, each of which is other than an oxygen atom or a halogen atom. Alternatively, the Group 10 atom can have an oxidation state of 0. Reaction of the precursor to produce the nanostructures is substantially catalytic RNA independent.

In one class of embodiments in which the Group 10 atom has an oxidation state of +2, the Group 10 atom is bonded to one or more carbon atoms (e.g., two or more carbon atoms). For example, the Group 10 atom can be bonded to two or more carbon atoms from 1,5-cyclooctadiene (COD). Such precursors include, but are not limited to, (COD)MRR', where M represents the Group 10 atom and where R and R' are independently selected from an alkyl group and an aryl group (e.g., R and R' can be equivalent aryl groups). Specific examples include dimethyl(1,5-cyclooctadiene)platinum(II) and dimethyl(1,5-cyclooctadiene)palladium(II) (i.e., $CODPtMe_2$ and $CODPdMe_2$, in which M is Pt or Pd and R and R' are methyl groups).

In one class of embodiments in which the Group 10 atom has an oxidation state of +2, the Group 10 atom is bonded to one or more phosphorus and/or arsenic atoms, e.g., to two or more phosphorus atoms, e.g., to two phosphine groups. Example precursors thus include $Pd(PR_3)_2Ar_2$, where R is an alkyl group or an aryl group and Ar is an aryl group, and $Pd(PAr_3)_2RR'$, where Ar is an aryl group and where R and R' are independently selected from an aryl group, a keto group, a thioketo group, and an amine group. For example, the precursor can be $Pd(PAr_3)_2Ar'_2$, where Ar and Ar' are independently selected aryl groups (e.g., ethoxybenzene or methoxybenzene groups, such that the precursor is $((C_6H_5)_3P)_2Pd(C_6H_4OEt)_2$ or $((C_6H_5)_3P)_2Pd(C_6H_4OMe)_2$. As another example, the precursor can be $Pd(PAr_3)_2Ar'(NR_2)$, $Pd(PAr_3)_2Ar'(NHR)$, or $Pd(PAr_3)_2Ar'(NH_2)$, where Ar and Ar' are independently selected aryl groups and where R is an alkyl group or an aryl group. Examples include $((C_6H_5)_3P)_2Pd(C_6H_5)(NAr''_2)$, where Ar'' is an aryl group, e.g., $((C_6H_5)_3P)_2Pd(C_6H_5)(Ntolyl_2)$. Yet other example precursors include $(DPPF)Pd(NR_2)Ar$, $(DPPF)Pd(NHR)Ar$, and $(DPPF)Pd(NH_2)Ar$, where DPPF is (diphenylphosphino)ferrocene, Ar is an aryl group, and R is an alkyl group or an aryl group.

In one class of embodiments in which the Group 10 atom has an oxidation state of 0, the Group 10 atom is bonded to one or more carbon atoms and/or one or more phosphorus atoms. For example, the Group 10 atom can be bonded to two or more carbon atoms from 1,5-cyclooctadiene (COD); e.g., the precursor can be $Pd(COD)_2$. Other exemplary precursors include those in which the Group 10 atom is bonded to one or more phosphine groups, e.g., tetrakis(triphenylphosphine)palladium(0) and tris(tri-tert-butylphosphine)palladium(0). Exemplary precursors also include tris(dibenzylidenacetone)dipalladium(0).

The precursor is typically reacted in the presence of at least a first surfactant to produce the nanostructures (and optionally also in the presence of a second, third, etc. surfactant and/or a non-coordinating solvent). The first surfactant can be a phosphine (e.g., a tri-alkylarylphosphine such as dodecylbenzylphosphine, or a bidentate phosphine such as diphenylphosphinopropane, diphenylphosphinoethane, or another diphenylphosphinoalkane). In other embodiments, the first surfactant is a thiol (e.g., an aryl thiol or an alkylaryl thiol).

The precursor is optionally reacted in the presence of a non-coordinating solvent to produce the nanostructures. The non-coordinating solvent optionally comprises an alkane or an alkene; for example, the non-coordinating solvent can be hexadecane, octadecane, octadecene, phenyldodecane, phenyltetradecane, or phenylhexadecane.

The precursor is optionally reacted to produce the nanostructures at a temperature greater than about 30° C., greater than about 50° C., greater than about 75° C., greater than about 100° C., greater than about 200° C., or even greater than about 300° C.

The nanostructures produced by the methods can be nanocrystals, substantially spherical nanocrystals, nanorods, branched nanostructures, and/or nanotetrapods.

Another general class of embodiments also provides methods for production of Group 10 metal nanostructures. In the methods, a precursor comprising a Group 10 atom selected from the group consisting of Pd, Pt, and Ni is provided. At least a first surfactant is also provided. The first surfactant is an aryl thiol, an alkylaryl thiol, or a phosphine other than a tri-n-alkylphosphine (e.g., a tri-alkylarylphosphine or a bidentate phosphine). The precursor is reacted in the presence of the first surfactant to produce the nanostructures. All of the features noted above apply to this embodiment as well, as applicable, e.g., for precursor composition, surfactant composition, inclusion of non-coordinating solvent(s), type of nanostructures produced, and the like.

In yet another general class of embodiments that provides methods for production of Group 10 metal nanostructures, the methods include providing a precursor and a reducing agent. The precursor comprises a Group 10 atom that is selected from the group consisting of Pd, Pt, and Ni and that has an oxidation state greater than zero. The precursor and the reducing agent are reacted in the presence of a phosphine or an arsine to produce the nanostructures.

In one class of embodiments, the Group 10 atom has an oxidation state of +2 or +4. The Group 10 atom is optionally bonded to at least one halogen atom, e.g., a halogen atom selected from the group consisting of Cl, Br, and I. Example precursors include Group 10 metal halides (e.g., palladium, platinum, or nickel chloride, bromide, or iodide) and compounds such as $H_2PtCl_6$. The reducing agent can be a hydride type reducing agent, e.g., sodium borohydride, sodium cyanoborohydride, or lithium aluminum hydride. The phosphine can be, e.g., a tri-n-alkylphosphine such as TOP, or more preferably, a tri-alkylarylphosphine such as dodecylbenzylphosphine. Similarly, alkyl, aryl, or alkylaryl arsines can be utilized. Bidentate phosphines (e.g., diphenylphosphinoalkanes) or bidentate arsines can also be used in the methods. All of the features noted above apply to this embodiment as well, as applicable, e.g., for phosphines, type of nanostructures produced, and the like.

Nanostructures produced by any of the methods of the invention form another feature of the invention. As noted, such nanostructures can be, e.g., nanocrystals, substantially spherical nanocrystals, nanorods, branched nanostructures, and/or nanotetrapods, and can include, e.g., small nanostructures and/or nanostructures having a narrow distribution of sizes.

Thus, one general class of embodiments provides a composition comprising a population of Group 10 metal nanostructures (e.g., Pd, Pt, or Ni nanostructures). The population exhibits a standard deviation in diameter of the nanostructures, which standard deviation is less than 20% of an average diameter of the nanostructures. The standard deviation is optionally less than 15% of the average diameter, or even less than 10% or less than 5% of the average diameter.

The nanostructures can be of essentially any size, but the average diameter is optionally less than 10.0 nm, and is preferably less than 5.0 nm or even less than 4.0 nm. Similarly, the nanostructures can be of essentially any shape. In one preferred class of embodiments, the nanostructures are substantially spherical.

Compositions produced by or useful in practicing the methods are also a feature of the invention. Thus, one general class of embodiments provides compositions including nanostructures and novel precursors of the invention. In this general class of embodiments, the composition includes a population of Group 10 metal nanostructures and a precursor comprising a Group 10 atom selected from the group consisting of Pd, Pt, and Ni. The Group 10 atom can have an oxidation state of +2 and be bonded to one or more atoms, each of which is other than an oxygen atom or a halogen atom. Alternatively, the Group 10 atom can have an oxidation state of 0. The composition is substantially free of any RNA whose presence increases a rate of reaction of the precursor to form the nanostructures by at least two fold.

The temperature of the composition can be greater than about 30° C. (e.g., greater than about 50° C., greater than about 75° C., greater than about 100° C., greater than about 200° C., or greater than about 300° C. or more). The composition optionally includes one or more surfactants and/or non-coordinating solvents. All of the features noted above apply to this embodiment as well, as applicable, e.g., for precursor composition, surfactant composition, non-coordinating solvent composition, nanostructure type, and the like.

Another general class of embodiments provides a composition including a population of Group 10 metal nanostructures and at least a first surfactant, wherein the first surfactant is an aryl thiol, an alkylaryl thiol, or a tri-alkylarylphosphine. All of the features noted above apply to this embodiment as well, as applicable, e.g., for type of nanostructures, surfactant composition, and the like.

Yet another general class of embodiments provides a composition that includes a precursor comprising a Group 10 atom selected from the group consisting of Pd, Pt, and Ni and at least a first surfactant. The first surfactant is a thiol or a phosphine other than a tri-n-alkylphosphine. In some embodiments, the Group 10 atom has an oxidation state of +2 and is bonded to one or more atoms each of which is other than an oxygen atom or a halogen atom. In other embodiments, the Group 10 atom has an oxidation state of 0.

The composition optionally also includes a non-coordinating solvent and/or a population of Group 10 metal nanostructures. All of the features noted above apply to this embodiment as well, as applicable, e.g., for precursor composition, type of nanostructures, surfactant composition, non-coordinating solvents, and the like.

Yet another general class of embodiments provides a composition comprising a precursor comprising a Group 10 atom selected from the group consisting of Pd, Pt, and Ni, which Group 10 atom has an oxidation state greater than zero; a reducing agent; a phosphine or an arsine; and a population of Group 10 metal nanostructures.

In one class of embodiments, the Group 10 atom has an oxidation state of +2 or +4. The Group 10 atom is optionally bonded to at least one halogen atom, e.g., a halogen atom selected from the group consisting of Cl, Br, and I. Example precursors include Group 10 metal halides (e.g., palladium, platinum, or nickel chloride, bromide, or iodide) and compounds such as $H_2PtCl_6$. In one class of embodiments, the reducing agent is a hydride type reducing agent, e.g., sodium borohydride, sodium cyanoborohydride, or lithium aluminum hydride.

The phosphine can be, e.g., a tri-n-alkylphosphine such as TOP, or more preferably, a tri-alkylarylphosphine such as dodecylbenzylphosphine. Similarly, alkyl, aryl, or alkylaryl arsines can be utilized. Bidentate phosphines (e.g., diphenylphosphinoalkanes) or bidentate arsines can also be used in the methods. All of the features noted above apply to this embodiment as well, as applicable, e.g., for type of nanostructures and the like.

BRIEF DESCRIPTION OF THE DRAWINGS

FIG. 1 schematically illustrates synthesis of palladium nanocrystals from $((C_6H_5)_3P)_2Pd(C_6H_5)(Ntolyl_2)$ (Panel A), $(COD)PdR_2$ (Panel B), and tetrakis(triphenylphosphine)palladium(0) (Panel C).

DEFINITIONS

Figure 2A:
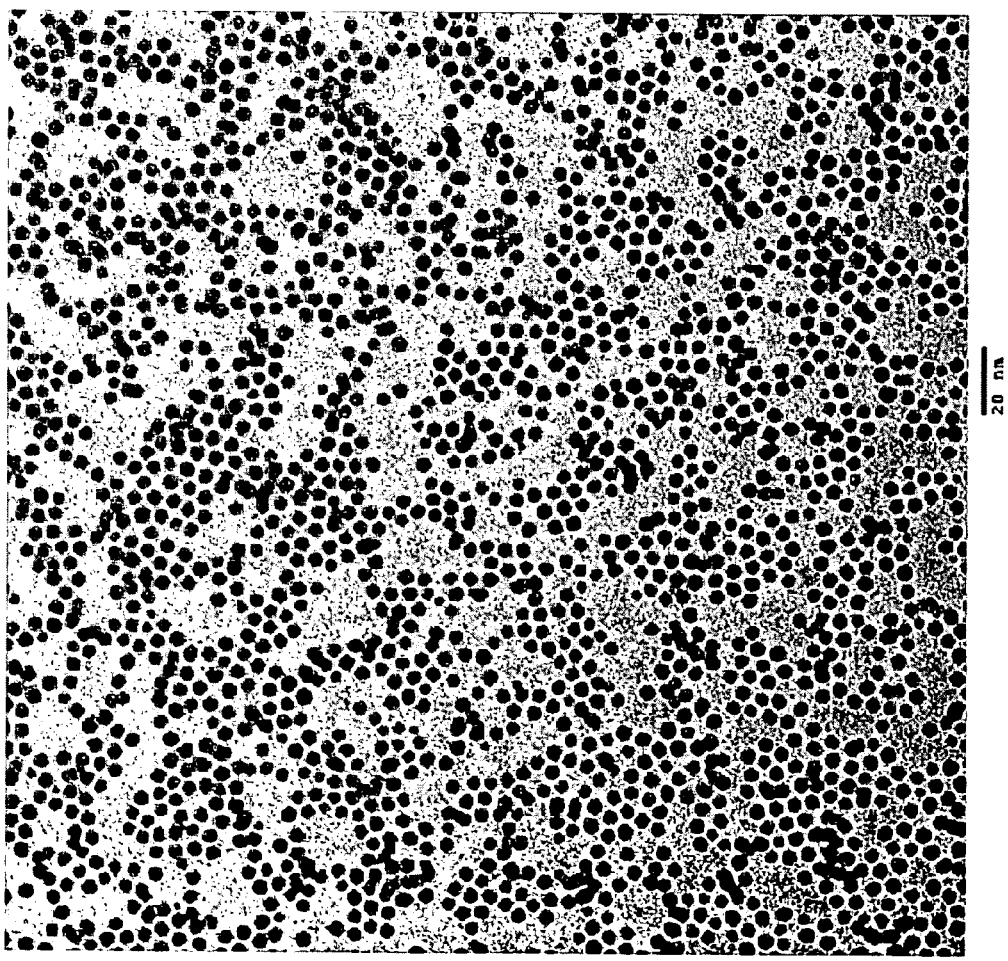
FIG. 2 Panel A shows a transmission electron micrograph of palladium nanocrystals. Panel B shows a transmission electron micrograph of palladium nanocrystals. Panel C presents results of XRD analysis of palladium nanocrystals.

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a nanostructure" includes a plurality of such nanostructures, and the like.

The term "about" as used herein indicates the value of a given quantity varies by +/−10% of the value, or optionally +/−5% of the value, or in some embodiments, by +/−1% of the value so described.

Two atoms are "bonded to" each other when they share a chemical bond, e.g., a covalent bond, a polar covalent bond, or an ionic bond.

An "alkyl group" refers to a linear (n-alkyl), branched, or cyclic saturated hydrocarbon moiety and includes all positional isomers. Alkyl groups can be, e.g., substituted or unsubstituted.

The term "aryl group" refers to a chemical substituent comprising or consisting of an aromatic group. Exemplary aryl groups include, e.g., phenyl groups, benzyl groups, tolyl groups, xylyl groups, alkyl-aryl groups, or the like. Aryl groups optionally include multiple aromatic rings (e.g., diphenyl groups, etc.). The aryl group can be, e.g., substituted or unsubstituted. In a "substituted aryl group", at least one hydrogen is replaced with one or more other atoms.

The term "alkyl-aryl group" refers to a group that comprises alkyl and aryl moieties.

An "amine group" has the formula RR'N—, where R and R' are independently selected from an organic group (e.g., an alkyl group, an aryl group, or the like) and a hydrogen.

A "keto group" has the formula RC(O)—, where R is an organic group (e.g., an alkyl group, an aryl group, or the like).

A "thioketo group" has the formula RC(S) —, where R is an organic group (e.g., an alkyl group, an aryl group, or the like).

A "thiol" has the formula RSH, where R is an organic group. Examples include, but are not limited to, an "aryl thiol", in which R is an aryl group, or an "alkylaryl thiol", in which R is an alkylaryl group.

A "phosphine" has the formula PRR'R", where R, R', and R" are independently an alkyl group, acyl group, aryl group (e.g., alkylaryl group), alkenyl group, alkynyl group, ester group, hydrogen, halide, or the like.

A "tri-n-alkyl phosphine" has the formula $PR_3$, where R is an n-alkyl group.

A "tri-alkylaryl phosphine" has the formula $PR_3$, where R is an alkylaryl group.

A "heteroatom" refers to any atom which is not a carbon or hydrogen atom. Examples include, but are not limited to, oxygen, nitrogen, sulfur, phosphorus, and boron.

A "nanostructure" is a structure having at least one region or characteristic dimension with a dimension of less than about 500 nm, e.g., less than about 200 nm, less than about 100 nm, less than about 50 nm, or even less than about 20 nm. Typically, the region or characteristic dimension will be along the smallest axis of the structure. Examples of such structures include nanowires, nanorods, nanotubes, branched nanostructures, nanotetrapods, tripods, bipods, nanocrystals, nanodots, quantum dots, nanoparticles, and the like. Nanostructures can be, e.g., substantially crystalline, substantially monocrystalline, polycrystalline, amorphous, or a combination thereof. In one aspect, each of the three dimensions of the nanostructure has a dimension of less than about 500 nm, e.g., less than about 200 nm, less than about 100 nm, less than about 50 nm, or even less than about 20 nm.

An "aspect ratio" is the length of a first axis of a nanostructure divided by the average of the lengths of the second and third axes of the nanostructure, where the second and third axes are the two axes whose lengths are most nearly equal each other. For example, the aspect ratio for a perfect rod would be the length of its long axis divided by the diameter of a cross-section perpendicular to (normal to) the long axis.

As used herein, the "diameter" of a nanostructure refers to the diameter of a cross-section normal to a first axis of the nanostructure, where the first axis has the greatest difference in length with respect to the second and third axes (the second and third axes are the two axes whose lengths most nearly equal each other). The first axis is not necessarily the longest axis of the nanostructure; e.g., for a disk-shaped nanostructure, the cross-section would be a substantially circular cross-section normal to the short longitudinal axis of the disk. Where the cross-section is not circular, the diameter is the average of the major and minor axes of that cross-section. For an elongated or high aspect ratio nanostructure, such as a nanowire or nanorod, a diameter is typically measured across a cross-section perpendicular to the longest axis of the nanowire or nanorod. For spherical nanostructures such as quantum dots, the diameter is measured from one side to the other through the center of the sphere.

The terms "crystalline" or "substantially crystalline," when used with respect to nanostructures, refer to the fact that the nanostructures typically exhibit long-range ordering across one or more dimensions of the structure. It will be understood by one of skill in the art that the term "long range ordering" will depend on the absolute size of the specific nanostructures, as ordering for a single crystal cannot extend beyond the boundaries of the crystal. In this case, "long-range ordering" will mean substantial order across at least the majority of the dimension of the nanostructure. In some instances, a nanostructure can bear an oxide or other coating, or can be comprised of a core and at least one shell. In such instances it will be appreciated that the oxide, shell(s), or other coating need not exhibit such ordering (e.g. it can be amorphous, polycrystalline, or otherwise). In such instances, the phrase "crystalline," "substantially crystalline," "substantially monocrystalline," or "monocrystalline" refers to the central core of the nanostructure (excluding the coating layers or shells). The terms "crystalline" or "substantially crystalline" as used herein are intended to also encompass structures comprising various defects, stacking faults, atomic substitutions, and the like, as long as the structure exhibits substantial long range ordering (e.g., order over at least about 80% of the length of at least one axis of the nanostructure or its core). In addition, it will be appreciated that the interface between a core and the outside of a nanostructure or between a core and an adjacent shell or between a shell and a second adjacent shell may contain non-crystalline regions and may even be amorphous. This does not prevent the nanostructure from being crystalline or substantially crystalline as defined herein.

The term "monocrystalline" when used with respect to a nanostructure indicates that the nanostructure is substantially crystalline and comprises substantially a single crystal. When used with respect to a nanostructure heterostructure comprising a core and one or more shells, "monocrystalline" indicates that the core is substantially crystalline and comprises substantially a single crystal.

A "nanocrystal" is a nanostructure that is substantially monocrystalline. A nanocrystal thus has at least one region or characteristic dimension with a dimension of less than about 500 nm, e.g., less than about 200 nm, less than about 100 nm, less than about 50 nm, or even less than about 20 nm. The term "nanocrystal" is intended to encompass substantially monocrystalline nanostructures comprising various defects, stacking faults, atomic substitutions, and the like, as well as substantially monocrystalline nanostructures without such defects, faults, or substitutions. In the case of nanocrystal heterostructures comprising a core and one or more shells, the core of the nanocrystal is typically substantially monocrystalline, but the shell(s) need not be. In one aspect, each of the three dimensions of the nanocrystal has a dimension of less than about 500 nm, e.g., less than about 200 nm, less than about 100 nm, less than about 50 nm, or even less than about 20 nm. Examples of nanocrystals include, but are not limited to, substantially spherical nanocrystals, branched nanocrystals, and substantially monocrystalline nanowires, nanorods, nanodots, quantum dots, nanotetrapods, tripods, bipods, and branched tetrapods (e.g., inorganic dendrimers).

A "substantially spherical nanocrystal" is a nanocrystal with an aspect ratio between about 0.8 and about 1.2.

A "nanorod" is a nanostructure that has one principle axis that is longer than the other two principle axes. Consequently, the nanorod has an aspect ratio greater than one. Nanorods of this invention typically have an aspect ratio between about 1.5 and about 10, but can have an aspect ratio greater than about 10, greater than about 20, greater than about 50, or greater than about 100, or even greater than about 10,000. Longer nanorods (e.g., those with an aspect ratio greater than about 10) are sometimes referred to as nanowires. The diameter of a nanorod is typically less than about 500 nm, preferably less than about 200 nm, more preferably less than about 150 nm, and most preferably less than about 100 nm, about 50 nm, or about 25 nm, or even less than about 10 nm or about 5 nm. Nanorods can have a variable diameter or can have a substantially uniform diameter, that is, a diameter that shows a variance less than about 20% (e.g., less than about 10%, less than about 5%, or less than about 1%) over the region of greatest variability. Nanorods are typically substantially crystalline and/or substantially monocrystalline, but can be, e.g., polycrystalline or amorphous.

A "branched nanostructure" is a nanostructure having three or more arms, where each arm has the characteristics of a nanorod, or a nanostructure having two or more arms, each arm having the characteristics of a nanorod and emanating from a central region that has a crystal structure distinct from that of the arms. Examples include, but are not limited to, bipods, tripods, and nanotetrapods (tetrapods).

A "nanotetrapod" is a generally tetrahedral branched nanostructure having four arms emanating from a central region or core, where the angle between any two arms is approximately 109.5 degrees. Typically, the core has one crystal structure and the arms have another crystal structure.

A "precursor" in a nanostructure synthesis reaction is a chemical substance (e.g., a compound or element) that reacts, e.g., with another precursor, and thereby contributes at least one atom to the nanostructure produced by the reaction.

Reaction of a precursor to produce nanostructures is "substantially catalytic RNA independent" when the rate of formation of the nanostructures in the absence of a catalytic RNA is at least 50% of the rate of formation of the nanostructures in the presence of the catalytic RNA (e.g., under reaction conditions which are otherwise equivalent). The rate of formation of the nanostructures in the absence of the catalytic RNA is preferably at least 75%, at least 90%, or at least 95%, more preferably at least 99%, and still more preferably is 100%, of the rate of formation of the nanostructures in the presence of the catalytic RNA.

A "surfactant" is a molecule capable of interacting (whether weakly or strongly) with one or more faces of a nanostructure and/or with one or more precursors used in producing the nanostructure.

A "non-coordinating solvent" is one that does not interact with one or more faces of a nanostructure and/or with one or more precursors used in producing the nanostructure. A typical weakly binding surfactant comprises a heteroatom having a free (non-bonded within the surfactant) pair of electrons, while a typical non-coordinating solvent does not include such a heteroatom and free pair of electrons.

A variety of additional terms are defined or otherwise characterized herein.

DETAILED DESCRIPTION

Methods for colloidal synthesis of Group 10 metal nanostructures, e.g., palladium (Pd) and platinum (Pt) nanostructures, have been described. Some of these methods use a precursor containing a metal-oxygen bond, e.g., bis(acetylacetonato)palladium(II) ($Pd(acac)_2$, Kim et al. (2003) "Synthesis of monodisperse palladium nanoparticles" Nano Letters 3:1289-1291). Other methods involve reduction of a halogen-containing metal compound such as $H_2PdCl_4$, $K_2PtCl_4$, or $H_2PtCl_6$ (Yee et al. (1999) One-phase synthesis of thiol-functionalized platinum nanoparticles" Langmuir 15:4314-4316; Ingelsten et al. (2001) "Kinetics of the formation of nano-sized platinum particles in water-in-oil microemulsions" J Colloid Interface Science 241:104-111; Ahmadi et al. (1996) "'Cubic' colloidal platinum nanoparticles" Chem Mater 8:1161-1163; and Ahmadi et al. (1.996) "Shape-controlled synthesis of colloidal platinum nanoparticles" Science 272: 1924-1926). The synthesis reactions typically include a surfactant such as trioctylphosphine (TOP) or octadecanethiol and/or a polymer (see, e.g., the references above, Son et al. (2004) "Facile synthesis of various phosphine-stabilized monodisperse palladium nanoparticles through understanding of coordination chemistry of the nanoparticles" Nano Letters 4:1147-1151, and Thomas and Kulkarni (2003) "From colloids to nanotechnology: Investigations of magic nuclearity palladium nanocrystals" Curr Sci 85:1760-1766). Such methods, however, can suffer from low yields and poor control over the size distribution of the resulting nanostructures. Such methods can also result in production of bulk metal rather than soluble metal nanostructures. Another method for synthesis of Pd nanoparticles is described in Gugliotti et al. (2004) "RNA-mediated metal-metal bond formation in the synthesis of hexagonal palladium nanoparticles" Science 304:850-852. This method, however, requires the use of a selected RNA to mediate metal-metal bond formation to achieve the synthesis of Pd nanoparticles from $Pd_2(DBA)_3$.

In one aspect, the present invention overcomes the above noted difficulties (e.g., the paucity of suitable precursors and precursor-surfactant combinations for synthesis of Group 10 metal nanostructures and the requirement for a catalytic RNA to be present in the synthesis reaction) by providing novel precursors, surfactants, and combinations thereof. Methods for producing Group 10 metal nanostructures are described, along with related compositions. The methods can, e.g., permit reproducible synthesis of Group 10 metal nanostructures, including, e.g., small nanostructures and/or populations of nanostructures having a narrow size distribution.

Precursors

One aspect of the invention provides novel precursors for the synthesis of Group 10 metal nanostructures, e.g., Pt, Pd, and Ni (nickel) nanostructures. The precursors include a Group 10 atom (Pd, Pt, or Ni) having an oxidation state of +2 or 0. As will be described in greater detail below, reaction of these precursors to form nanostructures does not require addition of a reducing agent or a synthetic or natural polymer (e.g., polyacrylamide, poly(vinylpyrrolidone), or RNA).

Metal(II) Precursors

In one aspect, precursors used to synthesize Group 10 metal nanostructures comprise a Group 10 atom (Pd, Pt, or Ni) having an oxidation state of +2. The Group 10 atom is bonded to one or more other atoms, each of which is other than an oxygen atom or a halogen atom (e.g., other than O, F, Cl, Br, or I).

The Group 10 atom can, for example, be bonded to one or more carbon atoms (e.g., to two or more carbon atoms). Alternatively or in addition, the Group 10 atom can be bonded to one or more (e.g., two or more) phosphorus and/or arsenic atoms, e.g., to one or two or more phosphine and/or arsine groups.

Example metal(II) precursors thus include precursors in which the Group 10 atom is bonded to two or more carbon atoms from 1,5-cyclooctadiene (COD). For example, the precursor can be (COD)MRR', where M represents the Group 10 atom and where R and R' are independently selected from an alkyl group and an aryl group. R and R' can be different or the same, alkyl groups, aryl groups, or combinations thereof; e.g., R and R' can be equivalent aryl groups. As two specific examples, M can be Pt or Pd while R and R' are methyl groups, such that the precursor is $CODPtMe_2$ or $CODPdMe_2$, i.e., dimethyl(1,5-cyclooctadiene)platinum(II) or dimethyl (1,5-cyclooctadiene)palladium(II).

Other example precursors include $Pd(PR_3)_2Ar_2$, where R is an alkyl group or an aryl group and Ar is an aryl group, and $Pd(PAr_3)_2RR'$, where Ar is an aryl group and where R and R' are independently selected from an aryl group, a keto group, a thioketo group, and an amine group. For example, the precursor can be $Pd(PAr_3)_2Ar'_2$, where Ar and Ar' are independently selected aryl groups. The two aryl groups can be distinct or identical chemical groups. As two specific examples, Ar and Ar' can be an ethoxybenzene or methoxybenzene group, such that the precursor is $((C_6H_5)_3P)_2Pd(C_6H_4OEt)_2$ or $((C_6H_5)_3P)_2Pd(C_6H_4OMe)_2$. As another example, the precursor can be $Pd(PAr_3)_2Ar'(NR_2)$, $Pd(PAr_3)_2Ar'(NHR)$, or $Pd(PAr_3)_2M(NH_2)$, where Ar and Ar' are independently selected aryl groups and where R is an alkyl group or an aryl group. More specific examples of this type precursor include $((C_6H_5)_3P)_2Pd(C_6H_5)(NAr''_2)$, where Ar'' is an aryl group, e.g., $((C_6H_5)_3P)_2Pd(C_6H_5)(Ntolyl_2)$.

Yet other example precursors include $(DPPF)Pd(NR_2)Ar$, $(DPPF)Pd(NHR)Ar$, and $(DPPF)Pd(NH_2)Ar$, where DPPF is (diphenylphosphino)ferrocene, Ar is an aryl group, and R is an alkyl group or an aryl group. Such precursors can be synthesized, e.g., from $PdCl_2$ or $(DPPF)PdCl_2$ by addition of aryl and/or amine substituents as described in Driver and Hartwig (1996) "A second-generation catalyst for aryl halide amination: Mixed secondary amines from aryl halides and primary amines catalyzed by $(DPPF)PdCl_2$)" J Am Chem Soc 118:7217-7218. It is worth noting that, for essentially any of the example precursors described herein that include Pd, equivalent precursors including Pt or Ni in place of Pd can be utilized.

Without intending to be limited to any particular mechanism, the metal(II) precursors described above can reductively eliminate the substituents from the metal atom, resulting in metal(0), the oxidation state of a Group 10 metal nanostructure. For example, the Pd (or Pt or Ni) precursors having Pd bonded to two carbons or to a carbon and a nitrogen can reversibly eliminate the corresponding substituents, resulting in a carbon-carbon or carbon-nitrogen bond and Pd(0). This contrasts with Pd (or Pt or Ni) compounds in which Pd is bonded to an oxygen or halogen atom (e.g., $Pd(acac)_2$), which are not optimum for such d10 metal reductive eliminations.

Such reductive elimination has been described in organometallic Stille and Heck coupling reactions and Pd-catalyzed reactions. See, e.g., Driver and Hartwig, supra; Louie and Hartwig (1995) "Palladium-catalyzed synthesis of arylamines from aryl halides. Mechanistic studies lead to coupling in the absence of tin reagents" Tetrahedron Lett 36:3609-3612; Wolfe and Buchwald (1996) "Palladium-catalyzed amination of aryl amines" J Org Chem 61:1133-1135; and Paul et al. (1994) "Palladium-catalyzed formation of carbon-nitrogen bonds. Reaction intermediates and catalyst improvements in the hetero cross-coupling of aryl halides and tin amides" J Am Chem Soc 116:5969-5970. However, although mechanistic detail about Pd metal centers in Pd-catalyzed reactions has been described, it has not previously been applied to assist in selection of precursors, reaction conditions, and the like for Pd nanostructure synthesis reactions, in which the Pd compounds are reactants rather than catalysts.

As one example, a Pd precursor with two equivalent triaryl phosphine and two aryl substituents or with two equivalent triaryl phosphine, one aryl, and one primary, secondary, or tertiary amine substituents bonded to the Pd metal center (e.g., $Pd(PAr_3)_2Ar'_2$, $Pd(PAr_3)_2Ar'(NH_2)$, $Pd(PAr_3)_2Ar'(NHR)$, or $Pd(PAr_3)_2Ar'(NR_2)$) can reductively eliminate to produce a Pd(0) nanostructure. Typically, the nanostructure synthesis reaction is performed in the presence of a surfactant, e.g., an excess of a phosphine or a thiol. The surfactant can be a tri-n-alkyl phosphine or, more preferably, a tri-alkylaryl phosphine such as dodecylbenzylphosphine; other examples are described herein or known in the art. A specific example is shown in FIG. 1 Panel A, which illustrates reaction of a $((C_6H_5)_3P)_2Pd(C_6H_5)(Ntolyl_2)$ precursor to form Pd nanocrystals by reductive elimination of an arylamine ($PhNtolyl_2$). In this example, the reaction occurs in the presence of trioctylphosphine (TOP), and the resulting nanocrystal has TOP associated with its surface (in equilibrium with the TOP that remains free in solution). Triphenylphosphine ($PPh_3$) is also formed.

Another example nanocrystal synthesis reaction is illustrated in FIG. 1 Panel B. In this example, heating $(COD)PdR_2$ in the presence of a surface ligand (i.e., a surfactant, L) results in elimination of the R groups, the dissociation of COD from the Pd, and formation of a Pd nanocrystal associated with the surfactant. The R group can be any alkyl or aryl group; in one embodiment, the R group is a methyl group, and the ethane byproduct can be evaporated. As described in U.S. Patent Application 60/628,455 filed Nov. 15, 2004 by Erik C. Scher et al. entitled "Process for group III-V semiconductor nanostructure synthesis and compositions made using same," such removal of a vaporous byproduct can increase yield of the resulting nanostructures.

Metal(0) Precursors

In another aspect, precursors used to synthesize Group 10 metal nanostructures comprise a Group 10 atom (Pd, Pt, or Ni) having an oxidation state of 0. The Group 10 atom is optionally bonded to one or more carbon atoms and/or one or more phosphorus atoms, e.g., to two or more carbon and/or phosphorus atoms.

Example metal(0) precursors thus include precursors in which the Group 10 atom is bonded to two or more carbon atoms from 1,5-cyclooctadiene (COD). For example, the precursor can be $Pd(COD)_2$. Example precursors also include those in which the metal is coordinated by dibenzylidenacetone (dba); e.g., the precursor can be tris(dibenzylideneacetone)dipalladium(0) ($Pd_2(dba)_3$), or it can be $Pd_2(dba)_3.P(o-tolyl)_3$ (which can be produced, e.g., from $Pd_2(dba)_3$ plus a phosphine and either isolated prior to reaction to form nanostructures or simply formed in situ in a reaction vessel and then reacted to form the nanostructures). Optionally, Pd(0) precursors of the invention exclude $Pd_2(dba)_3$.

Other example precursors include precursors in which the Group 10 atom is bonded to one or more phosphine groups (e.g., to two or three or more phosphines). For example, the precursor can be tris(tri-tert-butylphosphine)palladium(0), or it can be tetrakis(triphenylphosphine)palladium(0) (also known as palladium tetrakis). An exemplary reaction of palladium tetrakis to form Pd nanocrystals is schematically illustrated in FIG. 1 Panel C. The triphenylphosphine also formed by the reaction can associate with the surface of the nanocrystal (e.g., in equilibrium with the TOP or other surfactant used in the reaction). Without intending to be limited to any particular mechanism, such metal(0) precursors can exist in equilibrium with the metal(0) nanostructures. As noted previously, for essentially any of the example precursors described herein that include Pd, equivalent precursors including Pt or Ni in place of Pd can be utilized.

Surfactants and Non-Coordinating Solvents

As noted above, one or more surfactants are typically used in a nanostructure synthesis reaction, to assist in controlling shape and/or size of the resulting nanostructures, to maintain solubility and prevent aggregation of the nanostructures, and/or the like. A number of suitable surfactants are described herein and/or known in the art and can be used singly or in various combinations. Examples include, but are not limited to, tri-n-alkyl phosphines, tri-n-alkyl phosphine oxides, other phosphines and phosphine oxides, sulfonates, carboxylic acids, and thiols.

Suitable phosphines include tri-n-alkyl phosphines such as TOP and tri-n-butyl phosphine (TBP). Suitable phosphines also include tri-alkylarylphosphines such as dodecylbenzylphosphine. Use of a tri-alkylarylphosphine as a surfactant is preferred in some embodiments, since the phosphine is a "soft" ligand and thus preferable for "soft" d10 metals, the aryl group can pi-backbond from the metal, and the alkyl group can contribute to solubility in organic solvents. Exemplary phosphines also include bidentate phosphines, e.g., diphenylphosphinoalkanes such as diphenylphosphinopropane (DPPP) and diphenylphosphinoethane (DPPE). Other exemplary bidentate phosphines include DPPB, BDPF, BIPHEP, (−)-DIOP, (−)-BINAP and (R,R)-NORPHOS (see, e.g., Son et al. (2004) supra).

Thiols that can be used as surfactants include, but are not limited to, alkyl thiols, aryl thiols, and alkylaryl thiols, including, e.g., monothiols, dithiols, and the like. Use of aryl thiols or alkylaryl thiols as surfactants is preferred in some embodiments, since the thiol group is a "soft" ligand and thus preferable for "soft" d10 metals, the aryl group can pi-backbond from the metal, and/or the alkyl group can contribute to solubility in organic solvents. See, e.g., Adams et al. (1932) Org Syn Collect 1:504 and Pirmettis et al. (1996) "Synthesis and characterization of oxotechnetium(V) mixed-ligand complexes containing a tridentate N-substituted bis(2-mercaptoethyl)amine and a monodentate thiol" Inorg Chem 35:1685-1691.

A suitable surfactant (or combination of surfactants) for use with a given precursor can be determined by experimentation as is known in the art. Factors affecting choice of surfactant(s) can include, for example, reaction temperature, choice of precursor, and desired size and shape of the nanostructures to be produced. In certain embodiments, the same substance can serve as both a precursor and a surfactant, or the precursor can release a surfactant upon reacting to form the nanostructures. As noted, two or more surfactants can be used in a given synthesis reaction; for example, the precursor can be dissolved in TOP and injected into a larger volume of heated dodecylbenzylphosphine to initiate nanostructure growth.

In one aspect, nanostructures are synthesized by reacting precursors in the presence of one or more non-coordinating solvents. For example, a precursor can be reacted in the presence of a surfactant and a non-coordinating solvent; use of the non-coordinating solvent can, e.g., permit use of a smaller quantity and/or lower concentration of the surfactant, which can be advantageous. Suitable non-coordinating solvents include alkanes or alkenes (particularly long chain alkanes or alkenes), alkane substituted aryl derivatives, and the like. For example, hexadecane, octadecane, octadecene, phenyldodecane, phenyltetradecane, or phenylhexadecane can be used.

Methods for Producing Group 10 Metal Nanostructures

In one aspect, the invention provides methods for synthesizing nanostructures comprising a Group 10 metal. The methods make use of novel precursors, surfactants, or precursor-surfactant combinations. The resulting nanostructures (e.g., nanocrystals) can be of essentially any size and/or shape, including, e.g., substantially spherical nanocrystals (e.g., nanodots or quantum dots), nanorods, or branched nanostructures (e.g., bipods, tripods, or nanotetrapods).

One general class of embodiments provides methods for production of Group 10 metal nanostructures from novel precursors. In the methods, a precursor comprising a Group 10 atom selected from the group consisting of Pd, Pt, and Ni is provided and reacted to produce the nanostructures. In some embodiments, the Group 10 atom has an oxidation state of +2 and is bonded to one or more atoms, each of which is other than an oxygen atom or a halogen atom. In other embodiments, the Group 10 atom has an oxidation state of 0. Reaction of the precursor to produce the nanostructures is substantially catalytic RNA independent.

The precursor can be any of those described above in the sections entitled "Metal(II) Precursors" and "Metal(0) Precursors." The precursor is optionally reacted in the presence of one or more surfactants and/or non-coordinating solvents, e.g., any of those described herein.

A number of parameters can influence nanostructure growth and can be manipulated, independently or in combination, to control the size and/or shape distribution of the resulting nanostructures. These include, e.g., temperature (e.g., of nanostructure nucleation and/or growth), precursor composition, time-dependent precursor concentration, surfactant composition, surfactant concentration, number of surfactants, and ratio of surfactant(s) to each other and/or to the precursors. For example, precursor concentration can be adjusted to influence the shape of the nanostructures produced, e.g., by increasing or decreasing the amount of precursor initially provided, by introducing additional fresh precursor as the reaction progresses, or the like. As another example, the temperature can be controlled to control the shape and/or size distribution of the resulting nanostructures; e.g., nanostructure growth can be nucleated at a first, nucleation temperature and continued at a second, growth temperature.

The precursor is typically reacted at greater than ambient temperature. For example, the precursor can be reacted to produce the nanostructures at a temperature greater than about 30° C., greater than about 50° C., greater than about 75° C., greater than about 100° C., greater than about 200° C., or greater than about 300° C. or more.

Another general class of embodiments also provides methods for production of Group 10 metal nanostructures. In the methods, a precursor comprising a Group 10 atom selected from the group consisting of Pd, Pt, and Ni is provided. At least a first surfactant is also provided. The first surfactant is an aryl thiol, an alkylaryl thiol, or a phosphine other than a tri-n-alkylphosphine (e.g., a tri-alkylarylphosphine or a bidentate phosphine). The precursor is reacted in the presence of the first surfactant to produce the nanostructures.

The precursor can be any of those described herein, e.g., in the sections entitled "Metal(II) Precursors" and "Metal(0) Precursors." Similarly, the thiol or phosphine surfactant can be any of the corresponding type described herein. All of the features noted above apply to this embodiment as well, as applicable, e.g., for type of nanostructures produced and the like.

As noted above, such surfactants can be preferable to tri-n-alkylphosphines in certain embodiments. Synthesizing the nanostructures in the presence of such surfactants, as opposed to associating the surfactants with the nanostructures by exchange after synthesis of the nanostructures, can be advantageous in some instances. For example, although certain types of nanocrystals can be synthesized in the presence of TOP and then the TOP exchanged for another surfactant (e.g., Son et al., supra), such exchange can lead to deterioration of the nanocrystals (e.g., changes in their shape, broadening of their size distribution, and/or the like).

Yet another general class of embodiments provides methods for production of Group 10 metal nanostructures through reduction of a Group 10 atom. The methods include providing a precursor and a reducing agent. The precursor comprises a Group 10 atom that is selected from the group consisting of Pd, Pt, and Ni and that has an oxidation state greater than zero. The precursor and the reducing agent are reacted in the presence of a phosphine or an arsine to produce the nanostructures.

In one class of embodiments, the Group 10 atom has an oxidation state of +2 or +4. The Group 10 atom is optionally bonded to at least one halogen atom, e.g., a halogen atom selected from the group consisting of Cl, Br, and I. Example precursors include Group 10 metal halides (e.g., palladium, platinum, or nickel chloride, bromide, or iodide) and compounds such as $H_2PtCl_6$.

The reducing agent can be a hydride type reducing agent, e.g., sodium borohydride, sodium cyanoborohydride, or lithium aluminum hydride. These and a variety of other suitable reducing agents are commercially available or synthetically accessible.

The phosphine can be, e.g., any of those described herein; for example, the phosphine can be a tri-n-alkylphosphine such as TOP, or more preferably, a tri-alkylarylphosphine such as dodecylbenzylphosphine. Similarly, alkyl, aryl, or alkylaryl arsines can be utilized. Bidentate phosphines (e.g., diphenylphosphinoalkanes) or bidentate arsines can also be used in the methods. All of the features noted above apply to this embodiment as well, as applicable, e.g., for type of nanostructures produced and the like.

Nanostructures and Related Compositions

Nanostructures produced by any of the methods of the invention form another feature of the invention. As noted, such nanostructures can be, e.g., nanocrystals, substantially spherical nanocrystals, nanorods, branched nanostructures, and/or nanotetrapods. Also as noted, the methods of the invention can be used to produce small nanostructures and/or nanostructures having a narrow size distribution.

Thus, one general class of embodiments provides a composition comprising a population of Group 10 metal nanostructures (e.g., Pd, Pt, or Ni nanostructures). The population exhibits a standard deviation in diameter of the nanostructures, which standard deviation is less than 20% of an average diameter of the nanostructures. (For example, if the average diameter of the nanostructures is 5 nm, the standard deviation in diameter is less than 1 nm.) The standard deviation is optionally less than 15% of the average diameter, or even less than 10% or less than 5% of the average diameter.

The nanostructures can be of essentially any size, but the average diameter is optionally less than 10.0 nm, and is preferably less than 5.0 nm or even less than 4.0 nm. Similarly, the nanostructures can be of essentially any shape. In one preferred class of embodiments, the nanostructures are substantially spherical. A population of nanostructures typically includes at least 10 nanostructures, and more typically includes at least 100, at least $10^3$, at least $10^4$, or at least $10^5$ nanostructures.

Compositions produced by or useful in practicing the methods are also a feature of the invention. Thus, one general class of embodiments provides compositions including novel precursors of the invention and nanostructures. In this general class of embodiments, the composition includes a population of Group 10 metal nanostructures and a precursor comprising a Group 10 atom selected from the group consisting of Pd, Pt, and Ni. In some embodiments, the Group 10 atom has an oxidation state of +2 and is bonded to one or more atoms, each of which is other than an oxygen atom or a halogen atom. In other embodiments, the Group 10 atom has an oxidation state of 0. The composition can be substantially free of any RNA whose presence increases a rate of reaction of the precursor to form the nanostructures by at least two fold, and is optionally free of any RNA whose presence increases the rate by at least 1.33, 1.11, or 1.01 fold, or even free of any RNA whose presence measurably increases the rate. Alternatively or in addition, the temperature of the composition can be greater than about 30° C. (e.g., greater than about 50° C., greater than about 75° C., greater than about 100° C., greater than about 200° C., or greater than about 300° C. or more).

The precursor can be, e.g., any of those described above in the sections entitled "Metal(II) Precursors" and "Metal(0) Precursors" above. The composition optionally includes one or more surfactants (e.g., a phosphine or thiol) and/or non-coordinating solvents (e.g., an alkane or alkene), such as those described herein. The Group 10 nanostructures can be Pt, Pd, and/or Ni nanostructures, and can be, e.g., nanocrystals, substantially spherical nanocrystals, nanorods, branched nanostructures, and/or nanotetrapods. All of the features noted above apply to this embodiment as well, as applicable.

A related general class of embodiments provides compositions including novel surfactants of the invention and nanostructures. In these embodiments, the composition includes a population of Group 10 metal nanostructures and at least a first surfactant, wherein the first surfactant is an aryl thiol, an alkylaryl thiol, or a tri-alkylarylphosphine. The surfactant can be bound (i.e., associated with a surface of the nanostructure) and/or free. All of the features noted above apply to this embodiment as well, as applicable, e.g., for type of nanostructures, surfactant composition, and the like.

Another related general class of embodiments provides a composition including a population of Group 10 metal nanostructures and at least a first surfactant, wherein the composition is substantially free of TOP. The composition is optionally substantially free of tri-n-alkylphosphine. All of the features noted above apply to this embodiment as well, as applicable, e.g., for type of nanostructures, surfactant composition, and the like.

Another general class of embodiments provides a composition that includes a precursor comprising a Group 10 atom selected from the group consisting of Pd, Pt, and Ni and at least a first surfactant. The first surfactant is a thiol or a phosphine other than a tri-n-alkylphosphine. In some embodiments, the Group 10 atom has an oxidation state of +2 and is bonded to one or more atoms each of which is other than an oxygen atom or a halogen atom. In other embodiments, the Group 10 atom has an oxidation state of 0.

The precursor can be, e.g., any of those described above in the sections entitled "Metal(II) Precursors" and "Metal(0) Precursors" above. Similarly, the first surfactant can be any of those noted herein, e.g., a tri-alkylarylphosphine, a bidentate phosphine, an aryl thiol, or an alkylaryl thiol. The composition optionally also includes a non-coordinating solvent and/or a population of Group 10 metal nanostructures. All of the features noted above apply to this embodiment as well, as applicable, e.g., for type of nanostructures, surfactant composition, non-coordinating solvents, and the like.

Yet another general class of embodiments provides a composition comprising a precursor comprising a Group 10 atom selected from the group consisting of Pd, Pt, and Ni, which Group 10 atom has an oxidation state greater than zero; a reducing agent; a phosphine or an arsine; and a population of Group 10 metal nanostructures.

In one class of embodiments, the Group 10 atom has an oxidation state of +2 or +4. The Group 10 atom is optionally bonded to at least one halogen atom, e.g., a halogen atom selected from the group consisting of Cl, Br, and I. Example precursors include Group 10 metal halides (e.g., palladium, platinum, or nickel chloride, bromide, or iodide) and compounds such as $H_2PtCl_6$. In one class of embodiments, the reducing agent is a hydride type reducing agent, e.g., sodium borohydride, sodium cyanoborohydride, or lithium aluminum hydride.

The phosphine can be, e.g., any of those described herein; for example, the phosphine can be a tri-n-alkylphosphine such as TOP, or more preferably, a tri-alkylarylphosphine such as dodecylbenzylphosphine. Similarly, alkyl, aryl, or alkylaryl arsines can be utilized. Bidentate phosphines (e.g., diphenylphosphinoalkanes) or bidentate arsines can also be used in the methods. All of the features noted above apply to this embodiment as well, as applicable, e.g., for type of nanostructures and the like.

Any nanostructures of the invention can be modified, if desired, after they are produced. For example, any surfactant(s) coating the nanostructures can be exchanged for other surfactants or surface ligands. See, e.g., U.S. Patent Application 60/632,570 filed Nov. 30, 2004 and U.S. Patent Application Publication 20050109989.

Nanostructures produced by any of the methods herein can be incorporated into an optoelectronic device (e.g., a memory device) or nanocomposite, or can be used in essentially any other application in which Group 10 metal nanostructures are desired. Devices including nanostructures of the invention are also a feature of the invention.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. Accordingly, the following examples are offered to illustrate, but not to limit, the claimed invention.

Example 1

Synthesis of Palladium Nanocrystals

The following sets forth a series of experiments that demonstrate synthesis of palladium nanostructures, using a novel precursor and using a non-coordinating solvent to replace as much surfactant as possible in the reaction mixture. The resulting palladium nanocrystals have, e.g., a small average diameter and a narrow size distribution.

General Methods

All manipulations were carried out with strict exclusion of air and moisture by using Schlenk technique under an inert atmosphere of argon. Solvents and reagents were stored and handled in a glove box. Trioctylphosphine (TOP), min 97%, was obtained from Alfa Aesar and purified by distillation; the fraction with vapor temperature between 170 to 195° C. at <20 mtorr was collected. Octadecane was obtained from Aldrich and purified by distillation; the fraction with vapor temperature between 110 to 130° C. at <20 mtorr was collected. Tetrakis(triphenylphosphine)palladium(0) was obtained from Strem and used without further purification.

Synthesis of Pd Nanocrystals

Synthesis of Pd nanocrystals is schematically illustrated in FIG. 1 Panel C. To a 50 mL Schlenk flask was added trioctylphosphine (20 mL) and tetrakis(triphenylphosphine)palladium (0.400 g, 0.346 mmoles). A homogenous reagent solution was produced by heating on the Schlenk line to 70° C. for 60 minutes and then cooling the solution to room temperature. Next, a reaction solution was prepared by adding 64 mL octadecane to a 250 mL Schlenk flask; the flask was equipped with a thermocouple immersed in the reaction solution to monitor the solution temperature. The octadecane was heated with the temperature controller set to 320° C. The solution of tetrakis(triphenylphosphine)palladium in trioctylphosphine was then drawn into a 20 mL syringe through a 14 Gauge needle. When the octadecane solution reached 315° C., the contents of the syringe were quickly injected into the octadecane. Immediately the temperature controller was set to 300° C. Five minutes after the injection, the heat source was removed from the reaction flask and the reaction solution allowed to cool. When the solution temperature had reached about 60° C., the reaction solution was transferred into a vial and taken into the glove box for purification. Note that the nanocrystals should be purified immediately or the solution will solidify at room temperature.

Purification of Pd Nanocrystals

The reaction solution is transferred to eight 40 mL vials; each vial should have about 10 mL of reaction solution. To each vial 20 mL isopropyl alcohol is added and mixed extensively with a vortex mixer. If the solution appears to solidify, it is mixed further. Following centrifugation, the supernatant is decanted and the black precipitate retained for further purification. Again to each vial 20 mL isopropyl alcohol is added and mixed with the vortex mixer. Following centrifugation, the supernatant is decanted and the black precipitate retained for further purification. To each vial 20 mL ethyl alcohol is added and mixed with the vortex mixer. Following centrifugation, the supernatant is decanted and the black precipitate retained. All product is combined with toluene (4.0 mL) into one vial.

Analysis of Pd Nanocrystals

Figure 2B:
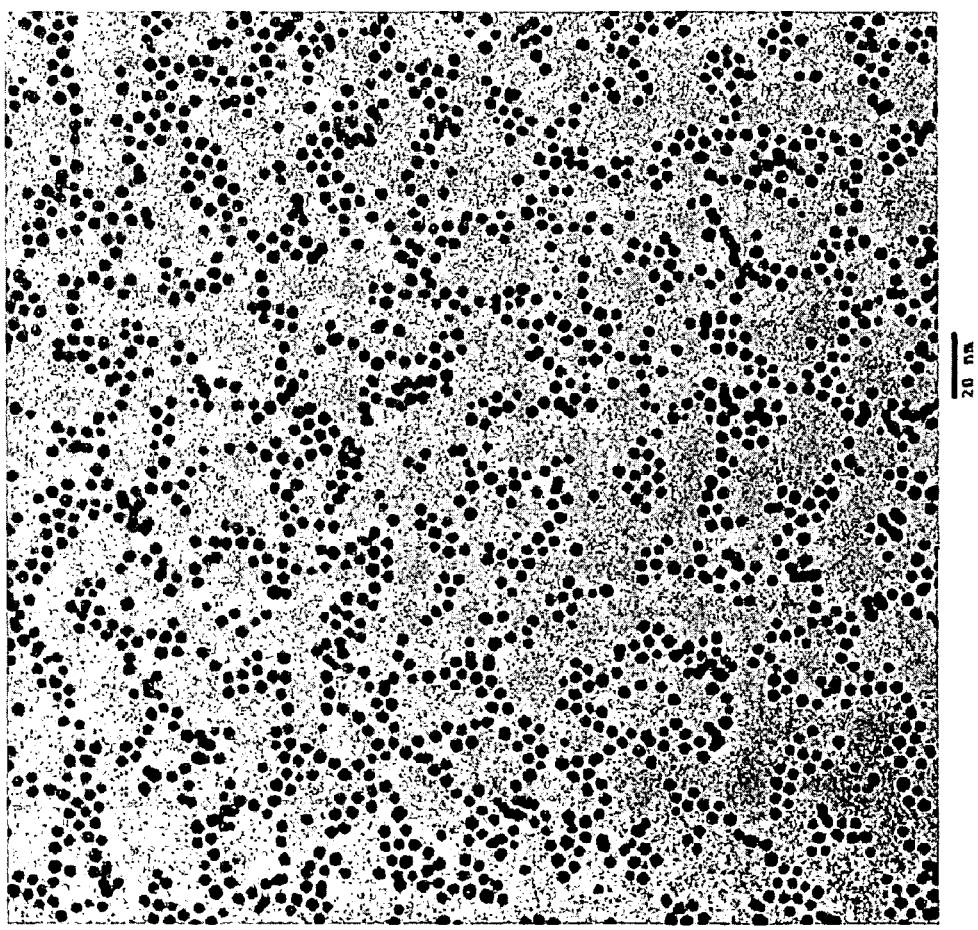
Figure 2C:
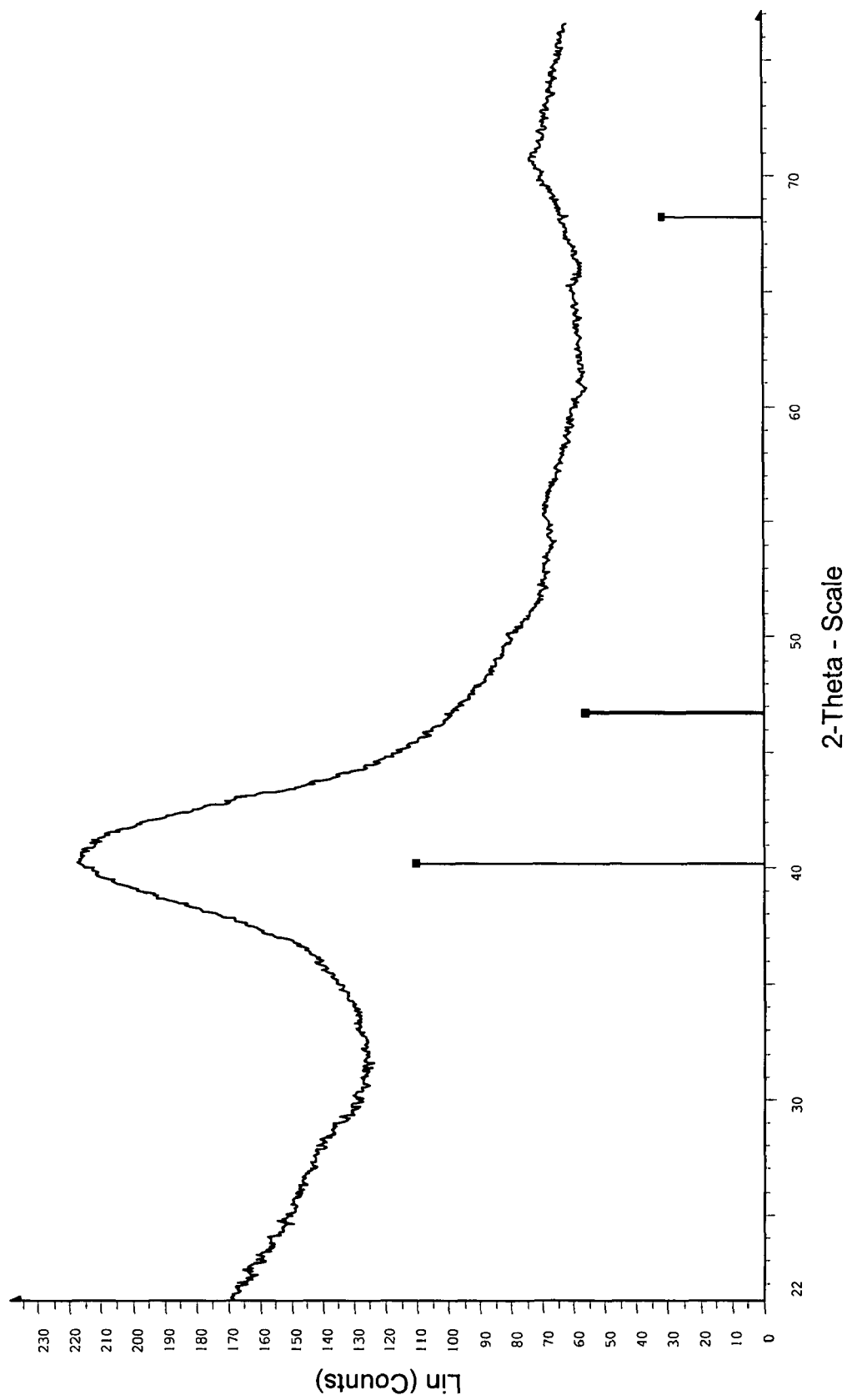

A transmission electron micrograph of the resulting Pd nanocrystals is shown in FIG. 2 Panel A. The average diameter of the nanocrystals is 4.00 nm and the standard deviation in diameter is 0.50, as determined by manual measurement of the nanocrystals on the image. Alternatively or in addition, the size distribution of the nanocrystals can be analyzed using software such as SIS image analysis software (Soft Imaging System GmbH, Münster, Germany).

A micrograph of smaller Pd nanocrystals is shown in FIG. 2 Panel B (average diameter 3.22 nm, standard deviation 0.49). These nanocrystals were obtained basically as described above but with a slower ramp in temperature after injection of the tetrakis(triphenylphosphine)palladium in TOP into the flask containing octadecane.

For powder X-ray diffraction (XRD), samples were dried to a powder on a quartz plate and run in a Bruker-AXS Discover D8 diffractometer with a general area detector diffraction system (GADDS). The x-ray source was Cu Kα radiation with a wavelength of 1.540598 Å. Theoretical lines were calculated using standard unit cell dimensions. XRD analysis of Pd nanocrystals is illustrated in FIG. 2 Panel C; theoretical lines are indicated by squares.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A nanostructure produced by a method for production of Group 10 metal nanostructures, the method comprising:
   providing a precursor, the precursor comprising a Group 10 atom selected from the group consisting of Pd, Pt, and Ni, wherein
   a) the Group 10 atom has an oxidation state of +2, the Group 10 atom being bonded to one or more atoms each of which is other than an oxygen atom or a halogen atom, or
   b) the Group 10 atom has an oxidation state of 0; and
   reacting the precursor to produce the nanostructures, wherein reaction of the precursor to produce the nanostructures is substantially catalytic RNA independent.

2. A nanostructure produced by a method for production of Group 10 metal nanostructures, the method comprising:
   providing a precursor comprising a Group 10 atom selected from the group consisting of Pd, Pt, and Ni, which Group 10 atom has an oxidation state greater than zero;
   providing a reducing agent; and
   reacting the precursor and the reducing agent in the presence of a phosphine or an arsine to produce the nanostructures.

3. A composition comprising:
   a precursor comprising a Group 10 atom selected from the group consisting of Pd, Pt, and Ni, wherein
   a) the Group 10 atom has an oxidation state of +2, the Group 10 atom being bonded to one or more atoms each of which is other than an oxygen atom or a halogen atom, or
   b) the Group 10 atom has an oxidation state of 0; and
   a population of Group 10 metal nanostructures;
   wherein the composition is substantially free of any RNA whose presence increases a rate of reaction of the precursor to form the nanostructures by at least two fold.

4. A composition comprising:
   a precursor comprising a Group 10 atom selected from the group consisting of Pd, Pt, and Ni, wherein
   a) the Group 10 atom has an oxidation state of +2, the Group 10 atom being bonded to one or more atoms each of which is other than an oxygen atom or a halogen atom, or
   b) the Group 10 atom has an oxidation state of 0; and
   at least a first surfactant, wherein the first surfactant is a thiol or a phosphine other than a tri-n-alkylphosphine.

5. A composition comprising:
   a precursor comprising a Group 10 atom selected from the group consisting of Pd, Pt, and Ni, which Group 10 atom has an oxidation state greater than zero;
   a reducing agent;
   a phosphine or an arsine; and
   a population of Group 10 metal nano structures.

6. A composition comprising:
   a population of Group 10 metal nanostructures selected from the group consisting of Pd, Pt, and Ni; and
   at least a first surfactant, wherein the first surfactant is an aryl thiol, an alkylaryl thiol, or a tri-alkylarylphosphine.

7. The composition of claim 6, wherein the nanostructures comprise one or more of: nanocrystals, substantially spherical nanocrystals, nanorods, branched nanostructures, or nanotetrapods.

8. A composition comprising a population of Group 10 metal nanostructures selected from the group consisting of Pd, Pt, and Ni, which population exhibits a standard deviation in diameter of the nanostructures which is less than 20% of an average diameter of the nanostructures.

9. The composition of claim 8, wherein the standard deviation is less than 15% of the average diameter.

10. The composition of claim 8, wherein the standard deviation is less than 10% of the average diameter.

11. The composition of claim 8, wherein the nanostructures are substantially spherical.

12. The composition of claim 8, wherein the average diameter is less than 5.0 nm.

13. The composition of claim 12, wherein the average diameter is less than 4.0 nm.

* * * * *